(12) United States Patent
Nishigaya et al.

(10) Patent No.: US 12,108,956 B2
(45) Date of Patent: Oct. 8, 2024

(54) HEMOSTATIC DEVICE

(71) Applicant: TERUMO KABUSHIKI KAISHA, Tokyo (JP)

(72) Inventors: Erika Nishigaya, Shizuoka (JP); Masako Miyashita, Fujinomiya (JP); Satoshi Nishimura, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 286 days.

(21) Appl. No.: 17/022,315

(22) Filed: Sep. 16, 2020

(65) Prior Publication Data

US 2021/0000476 A1 Jan. 7, 2021

Related U.S. Application Data

(63) Continuation of application No. PCT/IB2019/054392, filed on May 28, 2019.

(30) Foreign Application Priority Data

Mar. 30, 2018 (JP) .................................. 2018-068190

(51) Int. Cl.
*A61B 17/122* (2006.01)
*A61B 17/00* (2006.01)
(Continued)

(52) U.S. Cl.
CPC .......... *A61B 17/1325* (2013.01); *A61B 17/08* (2013.01); *A61B 17/122* (2013.01);
(Continued)

(58) Field of Classification Search
CPC .............. A61B 17/122; A61B 17/1325; A61B 17/0057; A61B 17/08; A61B 17/083;
(Continued)

(56) References Cited

U.S. PATENT DOCUMENTS

2004/0030335 A1* 2/2004 Zenati .............. A61B 17/12013
606/51
2005/0288707 A1 12/2005 De Canniere et al.
(Continued)

FOREIGN PATENT DOCUMENTS

CN 202761359 U 3/2013
JP 2008-504053 A 2/2008
(Continued)

OTHER PUBLICATIONS

An English-language version of the International Search Report (Form PCT/ISA/210) and the Written Opinion of the International Searching Authority (Form PCT/ISA/237) issued on Jul. 23, 2019, by the Japanese Patent Office in corresponding International Application No. PCT/IB2019/054392. (5 pages).
(Continued)

*Primary Examiner* — Sarah W Aleman
*Assistant Examiner* — Mikail A Mannan
(74) *Attorney, Agent, or Firm* — Buchanan Ingersoll & Rooney PC

(57) ABSTRACT

A hemostatic device is disclosed capable of effectively performing hemostasis on a puncture site of a subject without generating over-pressurization compression. The hemostatic device includes a first hemostatic member and a second hemostatic member which is movable relatively close to or away from the first hemostatic member, pinches a skin around the puncture site of the subject between the first hemostatic member and the second hemostatic member when the second hemostatic member moves toward the first hemostatic member, and performs hemostasis on the puncture site.

20 Claims, 11 Drawing Sheets

(51) Int. Cl.
  *A61B 17/08* (2006.01)
  *A61B 17/12* (2006.01)
  *A61B 17/132* (2006.01)
(52) U.S. Cl.
  CPC .. *A61B 17/132* (2013.01); *A61B 2017/00442* (2013.01); *A61B 2017/0065* (2013.01); *A61B 2017/00659* (2013.01); *A61B 2017/081* (2013.01); *A61B 17/083* (2013.01); *A61B 2017/12004* (2013.01)
(58) Field of Classification Search
  CPC ........ A61B 17/132; A61B 2017/00442; A61B 2017/0065; A61B 2017/00659; A61B 2017/081; A61B 2017/12004
  USPC .................................................. 606/131–133
  See application file for complete search history.

(56) References Cited

U.S. PATENT DOCUMENTS

| | | | | |
|---|---|---|---|---|
| 2008/0221504 | A1* | 9/2008 | Aghion | A61N 1/40 604/20 |
| 2011/0077647 | A1 | 3/2011 | Ambrosius et al. | |
| 2013/0006271 | A1 | 1/2013 | Vold et al. | |
| 2013/0237866 | A1* | 9/2013 | Cohen | A61B 5/02438 600/502 |
| 2014/0309687 | A1* | 10/2014 | Atkinson | A61B 17/083 606/218 |
| 2015/0088198 | A1* | 3/2015 | Spenciner | A61B 17/06166 606/232 |
| 2016/0066925 | A1 | 3/2016 | Van Sparrentak et al. | |
| 2016/0310155 | A1 | 10/2016 | Kimura et al. | |
| 2017/0165018 | A1* | 6/2017 | Hegeman | H04W 24/08 |
| 2018/0042615 | A1* | 2/2018 | Kimura | A61B 17/1325 |

FOREIGN PATENT DOCUMENTS

| | | | | |
|---|---|---|---|---|
| JP | 2008119517 | A | 5/2008 | |
| JP | 2015-502821 | A | 1/2015 | |
| JP | 2015-163173 | A | 9/2015 | |
| WO | 2014179830 | A1 | 11/2014 | |
| WO | 2016163326 | A1 | 10/2016 | |
| WO | 2017039006 | A1 | 3/2017 | |
| WO | WO2017/165108 | * | 9/2017 | ........... A61B 17/135 |

OTHER PUBLICATIONS

Office Action (Notice of Reasons for Refusal) issued Apr. 26, 2022, by the Japanese Patent Office in corresponding Japanese Patent Application No. 2018-068190 and an English Translation of the Office Action (6 pages).

International Search Report (PCT/ISA/210) and translation and Written Opinion (PCT/ISA/237) mailed on Jul. 23, 2019, by the Japanese Patent Office as the International Searching Authority for International Application No. PCT/IB2019/054392.

Office Action (Notice of Reasons for Refusal) issued Oct. 5, 2021, by the Japanese Patent Office in corresponding Japanese Patent Application No. 2018-068190 and an English Translation of the Office Action (8 pages).

* cited by examiner

HEMOSTATIC DEVICE

CROSS-REFERENCES TO RELATED APPLICATIONS

This application is a continuation of International Application No. PCT/IB2019/054392 filed on May 28, 2019, which claims priority to Japanese Application No. 2018-068190 filed on Mar. 30, 2018, the entire content of both of which is incorporated herein by reference.

FIELD OF THE DISCLOSURE

The present disclosure generally relates to a hemostatic device.

BACKGROUND DISCUSSION

In the related art, a manipulation of introducing various medical elongated bodies (for example, introducer) into a blood vessel of an arm of a patient via a puncture site formed in the blood vessel and performing a procedure or treatment on a lesion site is known. In a case where the manipulation is performed, an operator or the like performs hemostasis on the puncture site when the medical elongated body is removed from the puncture site.

As a hemostatic device which is used to perform the hemostasis on the puncture site, a hemostatic device is known, which includes a band for wrapping a limb such as an arm, securing means for securing the band in a state where the band wraps the limb, and a pressing portion which is interlocked to the band and is inflated by injecting a fluid to compress the puncture site (refer to Japanese Patent Application Publication No. 2008-119517 A).

In a hemostatic method using the hemostatic device described in Japanese Patent Application Publication No. 2008-119517 A, a compressing force is applied around the puncture site using an inflatable balloon. In the hemostatic method, if over-pressurization compression in which the compressing force increases excessively, arterial occlusion may occur. Accordingly, it is necessary to appropriately adjust the compressing force. Moreover, in a hemostatic method using a balloon, a gel, or the like, a compression range can be relatively large. Accordingly, a compressing force cannot be locally applied to the puncture site, and it may be difficult to increase a hemostasis effect.

SUMMARY

A hemostatic device is disclosed, which is capable of effectively performing hemostasis on the puncture site without generating the over-pressurization compression.

According to an aspect of the present disclosure, a hemostatic device is disclosed for performing hemostasis on a puncture site of a subject, the hemostatic device includes: a first hemostatic member; and a second hemostatic member which is movable relatively close to or away from the first hemostatic member and pinches a skin around the puncture site of the subject between the first hemostatic member and the second hemostatic member when the second hemostatic member moves toward the first hemostatic member.

According to the hemostatic device of the present disclosure, the skin around the puncture site of the subject is pinched between the first hemostatic member and the second hemostatic member, and thus, the hemostasis can be performed on the puncture site. Accordingly, the hemostatic device can rather effectively perform the hemostasis on the puncture site without generating over-pressurization compression.

In accordance with an aspect, a hemostatic device is disclosed, which is configured to perform hemostasis on a puncture site of a subject, the hemostatic device comprising: a first hemostatic member, a second hemostatic member, and a third hemostatic member; a support member; and an operation member configured to operate each of the first hemostatic member, the second hemostatic member, and the third hemostatic member in a radial direction.

In accordance with an another aspect, a method for performing hemostasis on a puncture site of a subject, the method comprising: moving a first hemostatic member toward a second hemostatic member, each of the first hemostatic member and the second hemostatic member including a rotatable roller; and pinching a skin around the puncture site of the subject between the first hemostatic member and the second hemostatic member.

DETAILED DESCRIPTION

Figure 1:
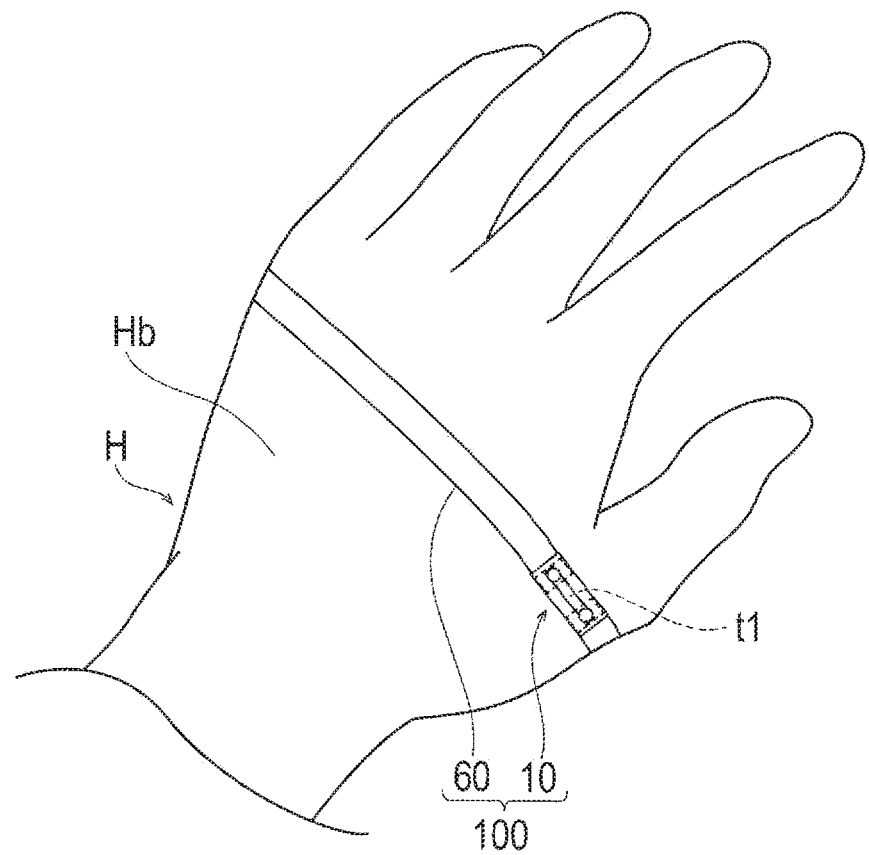
FIG. 1 is a view illustrating a state where a hemostatic device according to a first embodiment of the present disclosure is mounted on a hand of a subject.

Set forth below with reference to the accompanying drawings is a detailed description of embodiments of a hemostatic device representing examples of the inventive hemostatic device. Note that since embodiments described below are preferred specific examples of the present disclosure, although various technically preferable limitations are given, the scope of the present disclosure is not limited to the embodiments unless otherwise specified in the following descriptions. Moreover, in the drawings, the same reference signs are assigned to the same components, and detailed descriptions of the same reference signs assigned to the same components are appropriately omitted. In addition, dimensional ratios in the drawings are exaggerated for convenience of explanation, and may be different from the actual ratios.

First Embodiment

FIGS. 1 to 3C are views for explaining a hemostatic device 100 according to a first embodiment of the present disclosure.

For example, the hemostatic device 100 according to the present embodiment can be used to perform hemostasis on a puncture site t1 (hemostatic target site) formed on a radial artery (for example, a distal radial artery extending around a snuff box or to a fingertip side from the snuff box) of a palmar artery (deep palmar artery) extending to a dorsal side Hb of a hand H, for the purpose of inserting a treatment device such as a catheter performing a treatment, an inspection, or the like into a blood vessel of a subject, after removing an introducer indwelling in the puncture site t1. Note that a position where the puncture site t1 is formed may be any site such as a left hand, a right hand, a dorsal side of a hand, or a palm side of a hand. Moreover, the application of the hemostatic device 100 is not limited to only the hemostasis of the puncture site t1 formed on the hand H. For example, the hemostatic device 100 can be used to perform hemostasis on a puncture site formed in an arm of a subject for the purpose of inserting a medical device into a radial artery.

The hemostatic device 100 includes a hemostatic unit 10 and a securing unit 60, as described with reference to FIGS. 1 and 2. The details will be described below.

Hemostatic Unit

Figure 2:
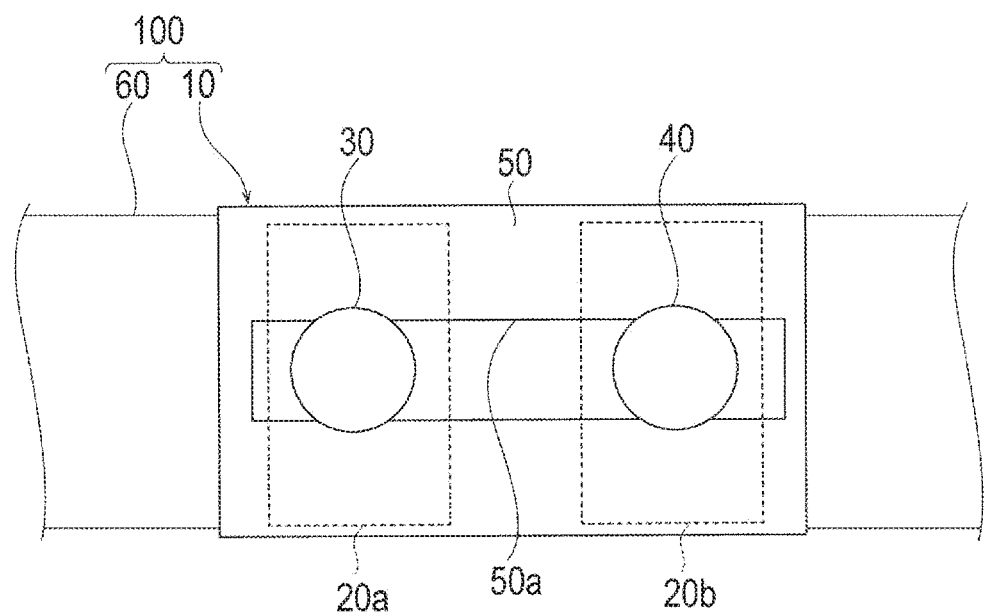
FIG. 2 is a plan view illustrating a first hemostatic member and a second hemostatic member according to the hemostatic device illustrated in FIG. 1.

As illustrated in FIG. 2, the hemostatic unit 10 includes a first hemostatic member 20a, a second hemostatic member 20b, shaft support members 30 and 40, and a plate-shaped member 50.

Hemostatic Member

Figure 3A:
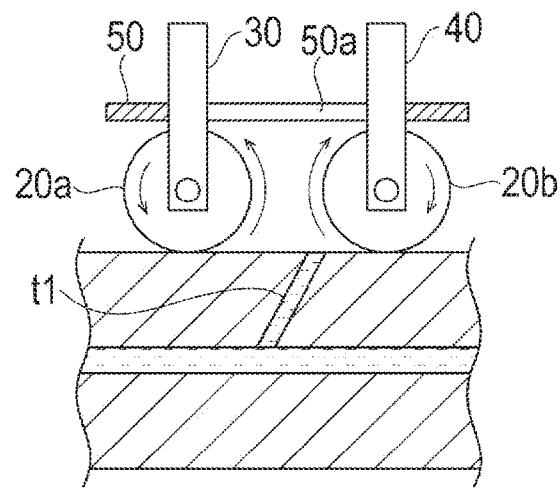
FIGS. 3A to 3C are cross-sectional views schematically illustrating a state where hemostasis is performed on a puncture site of the subject using the first hemostatic member and the second hemostatic member.
Figure 3B:
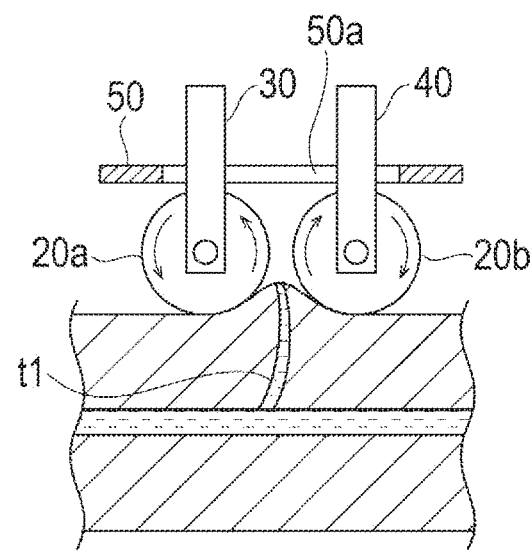
Figure 3C:
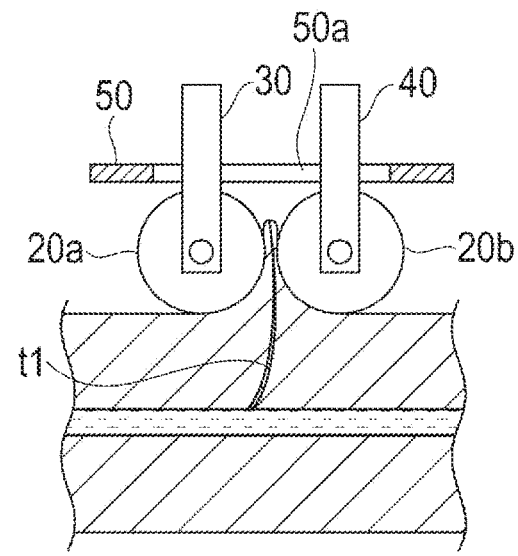
Figure 4:
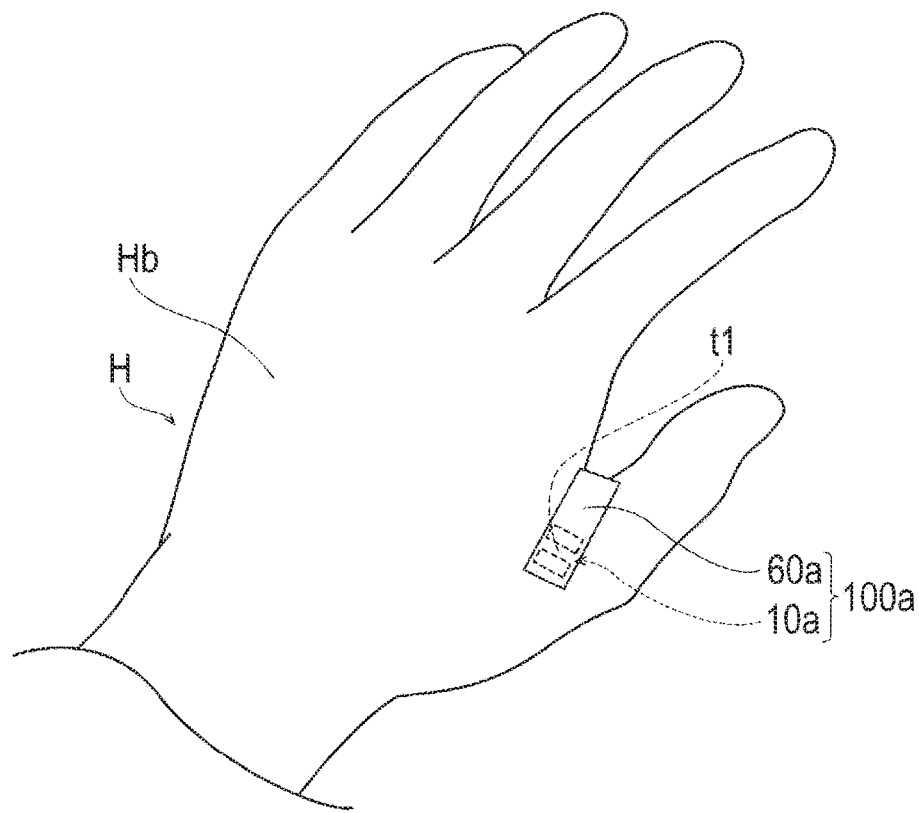
FIG. 4 is a view illustrating a state where a hemostatic device according to a second embodiment of the present disclosure is mounted on a hand of a subject.

As illustrated in FIGS. 3A to 3C, the first hemostatic member 20a and the second hemostatic member 20b are configured to move relatively close to and away from each other. As the second hemostatic member 20b moves close to (i.e., toward) the first hemostatic member 20a, the second hemostatic member 20b pinches a skin around the puncture site t1 of the subject between the first hemostatic member 20a and the second hemostatic member 20b. Accordingly, the hemostasis is performed on the puncture site t1. Each of the first hemostatic member 20a and the second hemostatic member 20b comprises a rotatable roller. For example, each of the first hemostatic member 20a and the second hemostatic member 20b can be formed of a relatively soft material such as rubber or elastomer, or a relatively hard material such as metal or plastic. For example, for a purpose of securing the skin without slipping while suppressing a pain when the skin is pinched between the first hemostatic member 20a and the second hemostatic member 20b, a surface of the rotatable roller of the first hemostatic member 20a and the second hemostatic member 20b can be formed of a rubber-like material or the like. Further, for a purpose of increasing a securing force to the skin, the surface of the roller can be formed of a relatively hard material such as a hard plastic or metal.

As illustrated in FIG. 3A, the shaft support member 30 rotatably supports the first hemostatic member 20a. The shaft support member 40 rotatably supports the second hemostatic member 20b. As illustrated in FIG. 2, each of the shaft support members 30 and 40 is movably attached to a hole 50a formed in the plate-shaped member 50. When the shaft support member 30 and the shaft support member 40 move relatively close to or away from each other, the first hemostatic member 20a supported by the shaft support member 30 and the second hemostatic member 20b supported by the shaft support member 40 move relatively close to or away from each other.

The plate-shaped member 50 is attached to the securing unit 60. As illustrated in FIG. 2, the plate-shaped member 50 may have a substantially rectangular shape in a plan view.

Each of the shaft support members 30 and 40 is configured such that a position of each of the shaft support members 30 and 40 with respect to the plate-shaped member 50 can be secured in a state where the skin around the puncture site t1 is pinched between the first hemostatic member 20a and the second hemostatic member 20b. For example, a securing mechanism for securing each of the shaft support members 30 and 40 to the plate-shaped member 50 can be, for example, a structure using a frictional force, a fitting structure using a groove, a movement/secure structure using a screw, or the like.

Securing Unit

The securing unit 60 secures the first hemostatic member 20a and the second hemostatic member 20b to the hand H of the subject. As illustrated in FIG. 1, the securing unit 60 may be a band-shaped member which can be attached to the hand H of the subject. The securing unit 60 wraps an outer periphery of the hand H so as to wrap around the hand. For example, the securing unit 60 can include a surface fastener for securing the securing unit 60. Moreover, the securing unit 60 may have an adhesive layer or the like which can be adhered to the skin of the subject and secured to the skin of the subject. The securing unit 60 is not limited to the band-shaped member and may, for example, include a glove structure configured to cover any finger of the hand H.

Use Example

Next, a use example of the hemostatic device 100 according to the present embodiment will be described.

An operator such as a doctor attaches the securing unit 60 to the hand H of the subject so that the securing unit 60 wraps the hand H in a state where the puncture site t1 is formed on the dorsal side Hb of the hand of the subject and an introducer sheath (not illustrated) is indwelled at the puncture site t1 (refer to FIG. 1).

After the operator removes the introducer sheath, as illustrated in FIG. 3A, the operator moves the first hemostatic member 20a and the second hemostatic member 20b so that the hemostatic members 20a and 20b are relatively close to each other while rotating the hemostatic members 20a and 20b. Accordingly, as illustrated in FIGS. 3B and 3C, the operator pulls the skin around the puncture site t1 by the first hemostatic member 20a and the second hemostatic member 20b, and thus, the skin can be pinched between the first hemostatic member 20a and the second hemostatic member 20b. Note that the operator may move the hemostatic members 20a and 20b before removing the introducer sheath.

The operator pinches the skin around the puncture site t1 between the hemostatic members 20a and 20b. Accordingly, the operator can close the puncture site t1 to locally perform the hemostasis on the puncture site t1 without applying a compressing force to the puncture site t1 as much as possible.

After the operator completes the hemostasis of the puncture site t1, the operator moves the hemostatic members 20a and 20b so that the hemostatic members 20a and 20b are relatively away from each other, and thus, releases the pinch of the skin around the puncture site t1.

As described above, the hemostatic device 100 according to the present embodiment includes the first hemostatic member 20a, and the second hemostatic member which can move relatively close to or away from the first hemostatic member 20a and pinches the skin around the puncture site t1 of the subject between the first hemostatic member 20a and the second hemostatic member 20b when the second hemostatic member 20b moves close to or toward the first hemostatic member 20a.

In the hemostatic device 100, the skin around the puncture site t1 of the subject is pinched between the first hemostatic member 20a and the second hemostatic member 20b, and thus, the hemostasis can be performed on the puncture site t1. Accordingly, the hemostatic device 100 can rather effectively perform the hemostasis on the puncture site t1 without generating over-pressurization compression. In a case where the hemostatic device 100 is used around a palmar artery, a skin of a distal radial artery rather easily stretches and a blood vessel extends at a relatively shallow position. Accordingly, hemostasis can be effectively performed on the site due to the pinch between the first hemostatic member 20a and the second hemostatic member 20b of the hemostatic device 100.

Moreover, each of the first hemostatic member 20a and the second hemostatic member 20b includes the rotatable roller. Accordingly, the skin around the puncture site t1 is pulled and pinched to be squeezed, and the hemostasis can be locally performed on the puncture site t1.

Moreover, the hemostatic device 100 includes the securing unit 60 which secures the first hemostatic member 20a and the second hemostatic member 20b to the hand H of the subject. Accordingly, it is possible to rather easily maintain a state where the hemostatic device 100 is secured to the hand H of the subject.

Moreover, the securing unit 60 is configured to include the band-shaped member which can be attached to the hand H of the subject. Accordingly, the hemostatic device 100 can be rather easily attached to the hand H.

Second Embodiment

FIGS. 4 to 6B are views for explaining a hemostatic device 100a according to a second embodiment. In the first embodiment, the securing unit 60 of the hemostatic device 100 may be the band-shaped member. However, for example, the securing unit can be configured as follows.

As illustrated in FIGS. 4 to 6B, the hemostatic device 100a includes a hemostatic unit 10a and a securing unit 60a. Note that descriptions of the substantially same configurations as those of the above-described embodiment are omitted.

The securing unit 60a is constituted by a holding member which pinches the hand H of the subject to secure the hemostatic device 100a to the hand H. In the present embodiment, the securing unit 60a has a clip structure which applies a securing force to the hand H by an elastic force, for example, of a material of the securing unit 60a.

Figure 5:
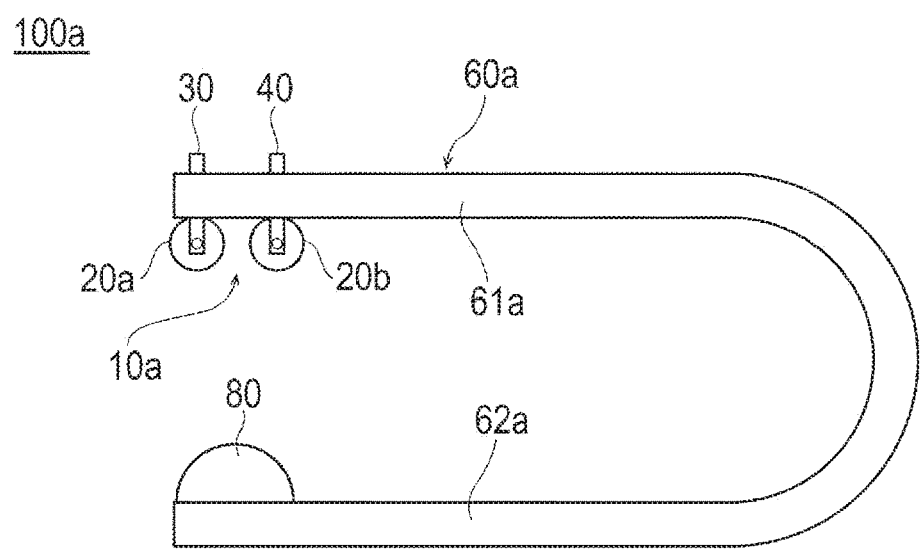
FIG. 5 is a side view of the hemostatic device illustrated in FIG. 4.

As illustrated in FIG. 5, the securing unit 60a has a substantially U-shaped cross section. Each of the hemostatic members 20a and 20b is disposed around an end portion of the securing unit 60a. The securing unit 60a pinches the hand H between a first holding portion 61a and a second holding portion 62a in a thickness direction of the hand H, and thus, the securing unit 60a is secured to the hand H.

In the securing unit 60a, a projection portion 80 projecting in a convex shape toward a side of each of the hemostatic members 20a and 20b is disposed at a position facing the hemostatic members 20a and 20b.

While the hemostasis is performed on the dorsal side Hb of the hand by the hemostatic members 20a and 20b, the projection portion 80 applies a pressing force from a palm side. Accordingly, it is possible to prevent the hemostatic device 100a from being displaced in a state where the hemostatic device 100a is secured to the hand H.

Figure 6A:
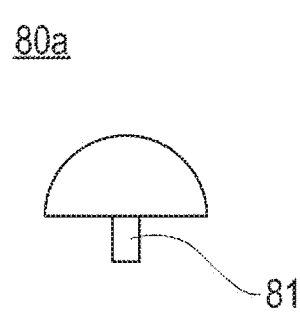
FIGS. 6A and 6B are views illustrating an example of a projection portion of the hemostatic device illustrated in FIG. 5.
Figure 6B:
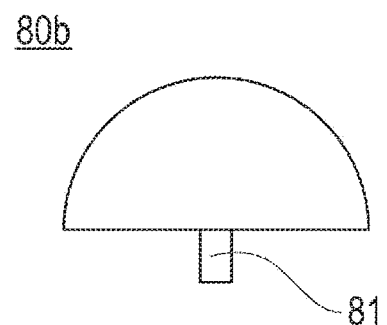

The projection portion 80 can be configured to be attached to or detached from the securing unit 60a. For example, as illustrated in FIGS. 6A and 6B, a plurality of projection portions 80a and 80b having different sizes may be prepared before a manipulation, and the projection portions 80a and 80b may be exchanged according to a size and shape of the hand H of the subject. Accordingly, it is possible to secure the hemostatic device 100a to the hand H of the patient regardless of the size of the hand H of the subject. For example, a securing shaft portion 81 is screwed to or fitted into a hole portion (not illustrated) formed in the securing unit 60a, and thus, each of the projection portions 80a and 80b can be connected to the securing unit 60a.

Note that the projection portion 80 can be attached to the securing unit 60 (refer to FIG. 1) by the above-described band-shaped member.

As described above, the hemostatic device 100a according to the present embodiment comprises the holding member in which the securing unit 60a pinches the hand H to secure the hemostatic device 100a. Accordingly, the hemostatic device 100a can be rather easily mounted on the hand H of the subject and secured to the hand H. Moreover, unlike the band-shaped member, the securing unit 60a is not disposed along the entire outer periphery of the hand H. Accordingly, a degree of freedom of the hand H of the subject increases while the hemostasis is performed. Moreover, unlike a glove, the hemostatic device 100a is not disposed so as to cover the entire hand H. Accordingly, it is possible to prevent the subject from feeling uncomfortable due to the hand H becoming hot and stuffy.

Moreover, the securing unit 60a is configured to include the projection portion 80 on the side opposite to the portions where the first hemostatic member 20a and the second hemostatic member 20b are disposed. Accordingly, it is possible to stably maintain the state where the hemostatic device 100a is secured to the hand H of the subject while the hemostasis is performed by the first hemostatic member 20a and the second hemostatic member 20b.

Figure 7:
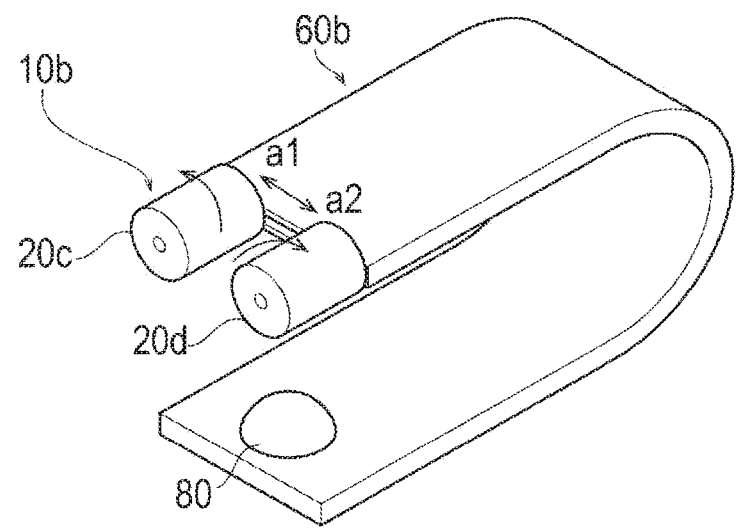
FIG. 7 is a perspective view illustrating Modification Example 1 of the hemostatic device according to the second embodiment.
Figure 8:
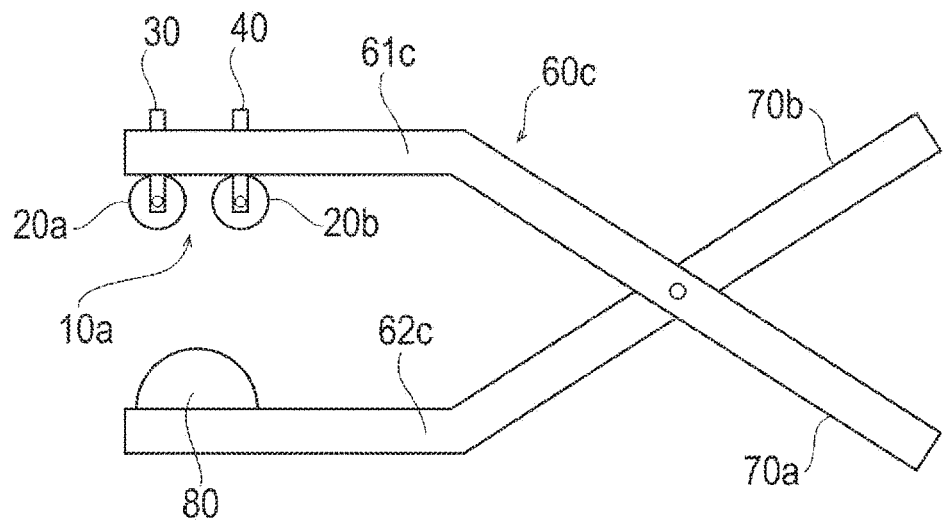
FIG. 8 is a side view illustrating Modification Example 2 of the hemostatic device according to the second embodiment.

FIG. 7 is a view illustrating a hemostatic device 100b according to Modification Example 1 of the second embodiment. FIG. 8 is a view illustrating a hemostatic device 100c according to Modification Example 2 of the second embodiment.

As illustrated in FIG. 7, in a securing unit 60b included in the hemostatic device 100b of Modification Example 1, a first hemostatic member 20c and a second hemostatic member 20d are disposed to project outward from an end portion of the securing unit 60b. In FIG. 7, the first hemostatic member 20c and the second hemostatic member 20d are supported in a cantilever manner and are configured to be movable relatively close to or away from each other in directions indicated by an arrow a1-a2.

As illustrated in FIG. 8, a securing unit 60c included in the hemostatic device 100c of Modification Example 2 is configured as follows. The operator or the like grips grip portions 70a and 70b and moves a first holding portion 61c and a second holding portion 62c pivotally connected to each other so that the first holding portion 61c and the second holding portion 62c are close to each other, and thus, the hemostatic device 100c can be attached to the hand H. While the operator or the like holds the grip portions 70a and 70b, it is possible to maintain securing of the hemostatic device 100c with respect to the hand H.

Third Embodiment

Figure 9:
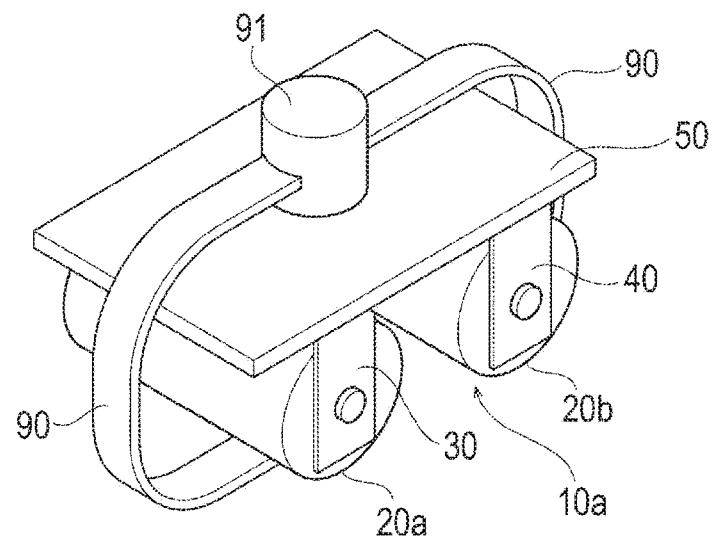
FIG. 9 is a perspective view illustrating a hemostatic device according to a third embodiment of the present disclosure.
Figure 10:
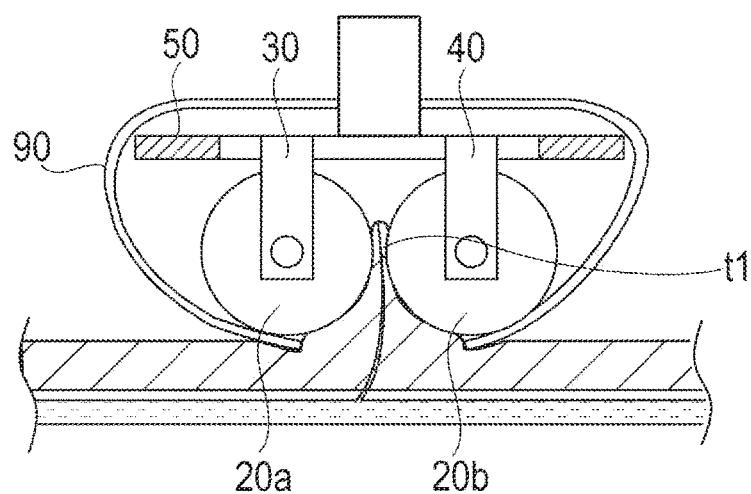
FIG. 10 is a cross-sectional view schematically illustrating a state where hemostasis is performed on a puncture site of a subject using the hemostatic device illustrated in FIG. 9.

FIGS. 9 and 10 are views for explaining a hemostatic device 100d according to a third embodiment.

As illustrated in FIG. 9, a hemostatic unit 10a of the hemostatic device 100d includes the first hemostatic member 20a, the second hemostatic member 20b, the shaft support members 30 and 40, the plate-shaped member 50, and an arm portion 90. Although not illustrated, the hemostatic unit 10a is attached to the securing unit 60 (refer to FIG. 1).

The shaft support members 30 and 40 are movably attached to the plate-shaped member 50, and as illustrated in FIG. 9, the plate-shaped member 50 has the arm portion 90 which is attached via a cylindrical member 91.

The arm portion 90 pinches the skin around the hemostatic target site t1 from the outside of the first hemostatic member 20a and the second hemostatic member 20b. In the present embodiment, the arm portion 90 may be a curved flat plate member. Note that a specific shape, a material of the arm portion, or the like of the arm portion 90 is not limited.

As illustrated in FIG. 10, the arm portion 90 pinches the skin around the puncture site t1 pulled by the first hemostatic member 20a and the second hemostatic member 20b from the outside of each of the hemostatic members 20a and 20b. Accordingly, in the hemostatic device 100d, the skin around the puncture site t1 can be locally held by the arm portion 90 together with each of the hemostatic members 20a and 20b, and thus, it is possible increase a hemostasis effect. As illustrated in FIG. 10, the arm portion 90 performs the pinching so as to close a hole of a blood vessel wall. Accordingly, it is possible to quickly perform the hemostasis.

Fourth Embodiment

Figure 11A:
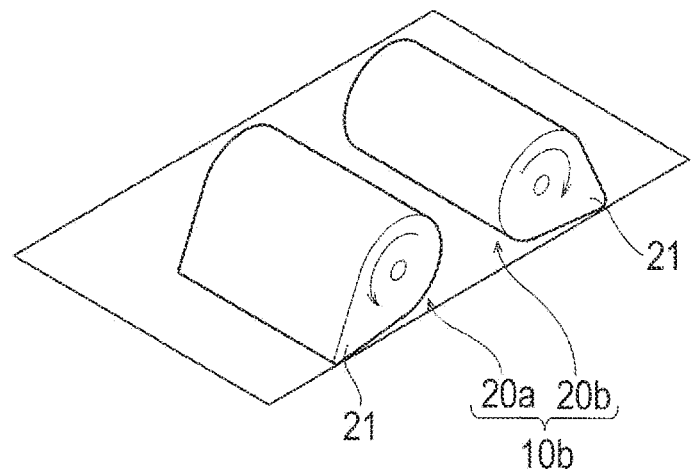
FIGS. 11A to 11C are perspective views schematically illustrating an operation example of a hemostatic device according to a fourth embodiment of the present disclosure.
Figure 11B:
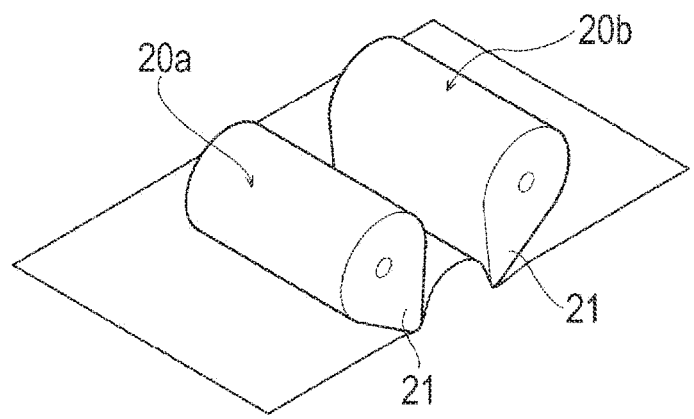
Figure 11C:
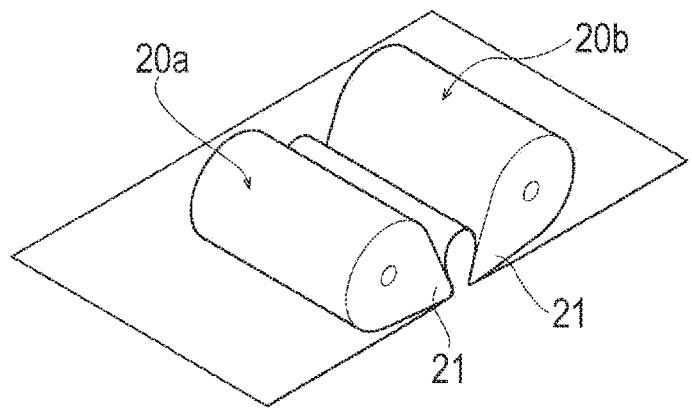

FIGS. 11A to 11C are views schematically illustrating a portion of a hemostatic device according to a fourth embodiment of the present disclosure.

In the hemostatic device according to the fourth embodiment, a convex portion 21 is formed on the first hemostatic member 20a by a roller. Further, the convex portion 21 is also formed on the second hemostatic member 20b composed of a roller. The convex portion 21 is formed in a portion of each of the hemostatic members 20a and 20b in a circumferential direction of the hemostatic members 20a and 20b, and projects outward of each of the hemostatic members 20a and 20b in a radial direction of the hemostatic members 20a and 20b.

The convex portion 21 is formed along the entire longitudinal direction of each of the hemostatic members 20a and 20b. Moreover, the convex portion 21 is integrally formed with each of the hemostatic members 20a and 20b.

As illustrated in FIG. 11A, in the hemostatic device according to the fourth embodiment, the first hemostatic member 20a and the second hemostatic member 20b are disposed so as to pinch a puncture site (not illustrated). In this case, as illustrated in FIG. 11A, the convex portion 21 of the first hemostatic member 20a and the convex portion 21 of the second hemostatic member 20b are disposed so as to face outward (i.e., away from each other). Then, as illustrated in FIG. 11B, the first hemostatic member 20a and the second hemostatic member 20b are rotated, and the skin around the puncture site is pinched by the convex portions 21. The hemostatic device holds the skin around the puncture site in a narrow range by the convex portion 21 of the first hemostatic member 20a and the convex portion 21 of the second hemostatic member 20b. Therefore, the hemostatic device according to the present embodiment can increase the hemostasis effect.

Figure 12A:
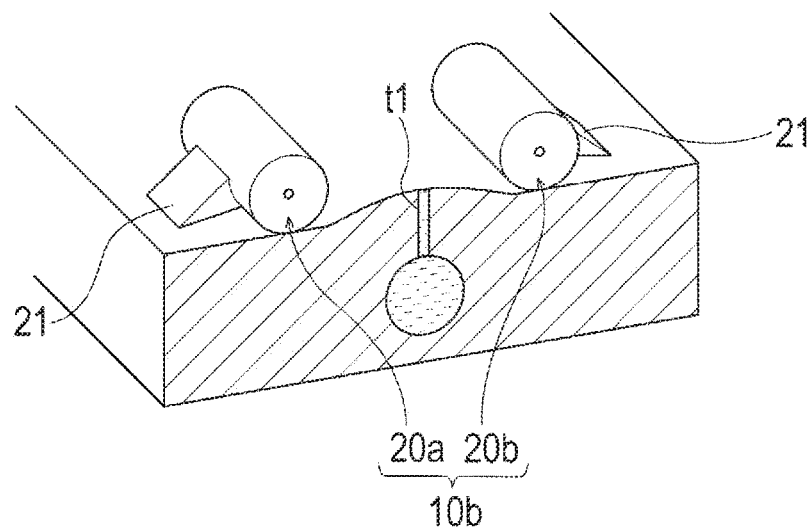
FIGS. 12A to 12C are perspective views schematically illustrating an operation example of a hemostatic device according to Modification Example of the fourth embodiment.
Figure 12B:
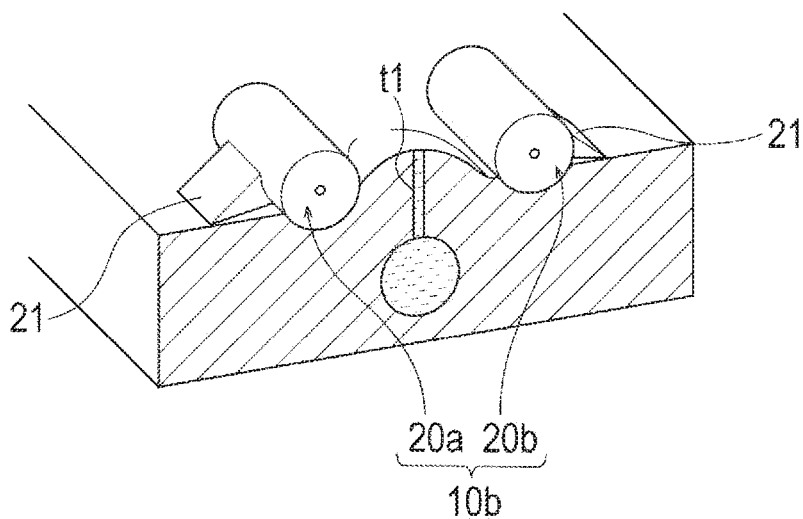
Figure 12C:
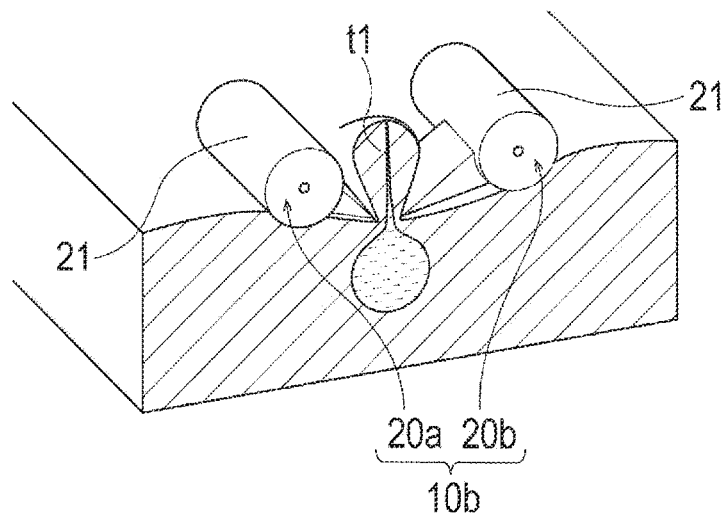

FIGS. 12A to 12C are views illustrating a hemostatic device according to a modification example of the fourth embodiment. The convex portion 21 does not need to be formed over the entire length of each of the hemostatic members 20a and 20b in the longitudinal direction. As illustrated in the present modification example, for example, the convex portion 21 can be formed in a portion of each of the hemostatic members 20a and 20b in the longitudinal direction. The convex portions 21 are provided in this manner, and thus, it is possible to locally apply a holding force in a relatively narrower range. Accordingly, it is possible to increase the hemostasis effect of the hemostatic device. Moreover, the hole of the blood vessel wall is pinched so as to be closed by the convex portions 21, and thus, it is possible to quickly perform the hemostasis as in the above. In addition, it is possible to prevent the holding force from being applied to a site where the hemostasis is unnecessary.

Fifth Embodiment

Figure 13A:
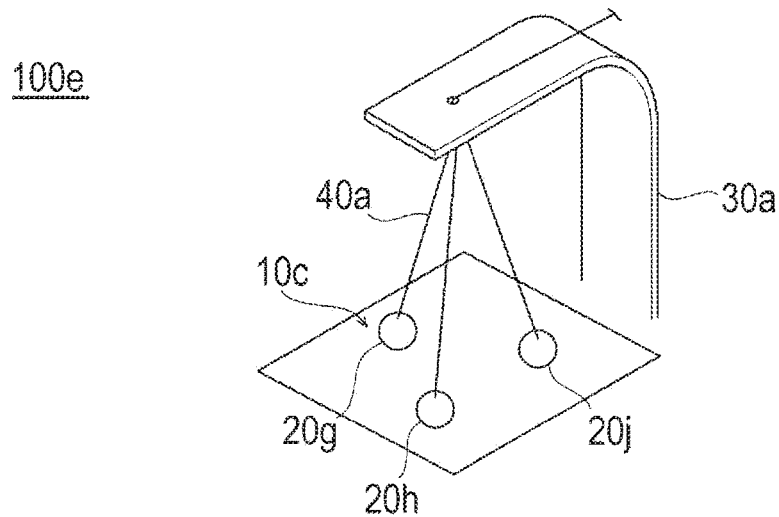
FIGS. 13A to 13C are perspective views schematically illustrating an operation example of a hemostatic device according to a fifth embodiment of the present disclosure.
Figure 13B:
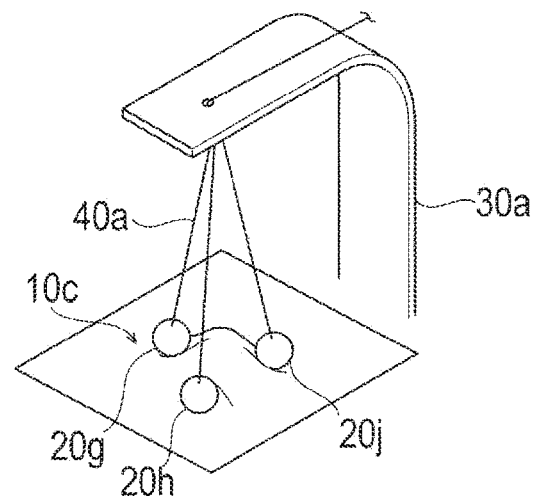
Figure 13C:
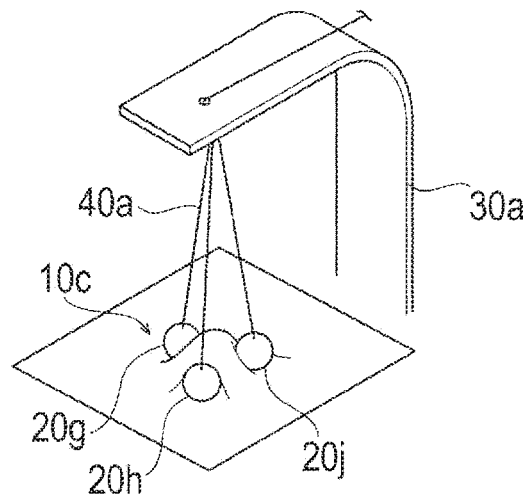

FIGS. 13A to 13C are views for explaining a hemostatic device 100e of a fifth embodiment of the present disclosure.

As illustrated in FIG. 13A, the hemostatic device 100e according to the present embodiment has a hemostatic unit 10c. The hemostatic unit 10c includes a first hemostatic member 20g, a second hemostatic member 20h, a third hemostatic member 20j, a support member 30a, and an operation member 40a for operating relative approach and separation of the hemostatic members 20g, 20h, and 20j.

The first hemostatic member 20g, the second hemostatic member 20h, and the third hemostatic member 20j are configured to be movable not in one direction but in a radial direction, as illustrated in FIGS. 13A to 13C. As a result, a skin located around a puncture site (not illustrated) is pulled and pinched, and hemostasis is locally performed on the puncture site. Each of the first hemostatic member 20g, the second hemostatic member 20h, and the third hemostatic member 20j is formed in a substantially spherical shape in the present embodiment. However, specific shapes of the first hemostatic member 20g, the second hemostatic member 20h, and the third hemostatic member 20j are not limited. Further, a material of each of the first hemostatic member 20g, the second hemostatic member 20h, and the third hemostatic member 20j is not limited. For example, the material of the first hemostatic member 20g, the second hemostatic member 20h, and the third hemostatic member 20j may include a resin material such as rubber.

The support member 30a may be a bent plate-shaped member which supports the first hemostatic member 20g, the second hemostatic member 20h, and the third hemostatic member 20j.

Each of the hemostatic members 20g, 20h, and 20j is connected to the string-shaped operation member 40a. When the operation member 40a is operated to be gripped and pulled, the hemostatic members 20g, 20h, and 20j move relatively close to each other. Further, when the pulling is released, the operation member 40a moves the hemostatic members 20g, 20h, and 20j so that the hemostatic members 20g, 20h, and 20j are moved relatively away from each other. When the operator operates the operation member 40a so that the hemostatic members 20g, 20h, 20j are close to each other, a skin near a center position when the hemostatic members 20g, 20h, 20j are close to each other is pinched. Accordingly, it is possible to locally perform hemostasis on the puncture site.

Hereinbefore, as described in the present modification example, the number of hemostatic members provided in the hemostatic device is not limited to two. Further, a method of pinching the skin by the hemostatic members is not limited to the method using the roller.

Other Hemostatic Methods

In a hemostatic method using the hemostatic device according to the present disclosure, for example, an embolization material or the like can be used together with the hemostatic device. Hereinafter, an example of the hemostatic method will be described.

Figure 14:
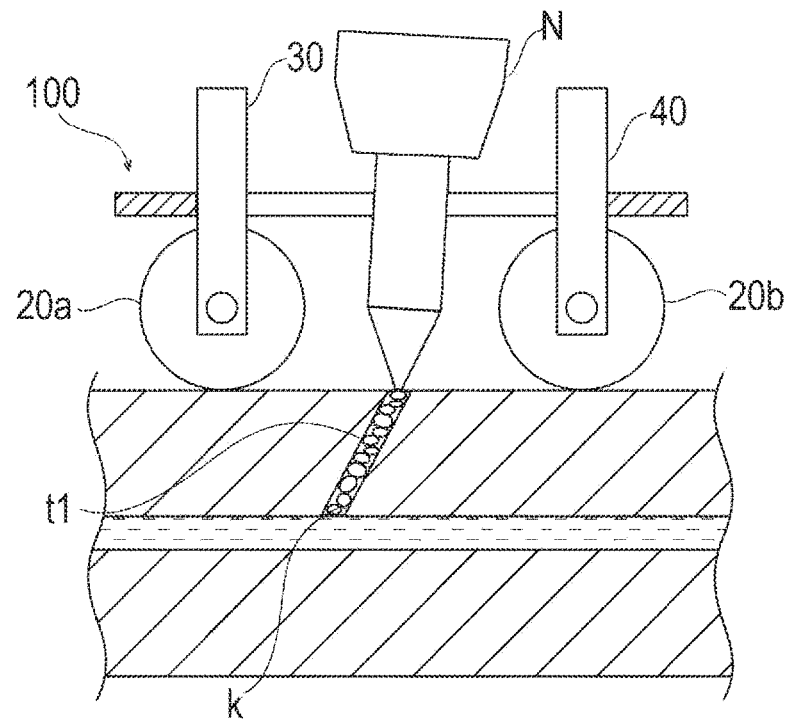
FIG. 14 is a cross-sectional view schematically illustrating an example of a hemostatic method using the hemostatic device according to the present disclosure.

For example, as illustrated in FIG. 14, after an embolization material k is disposed in the puncture site t using an applicator N capable of discharging the embolization material k, it is possible to perform hemostasis using the hemostatic device 100. In this case, the hemostasis can be performed more quickly in the same manner as described above while closing the hole in the blood vessel wall by the embolization material k.

Figure 15:
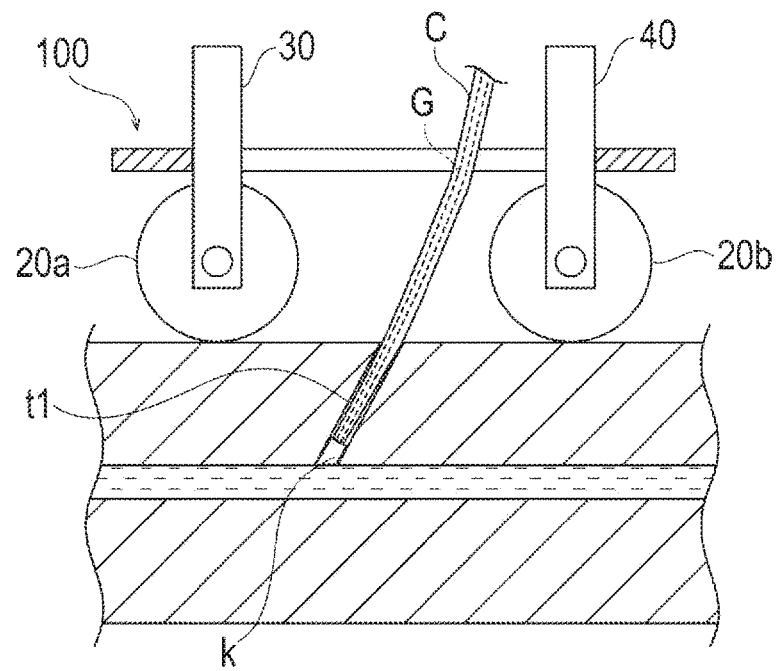
FIG. 15 is a cross-sectional view schematically illustrating an example of the hemostatic method using the hemostatic device according to the present disclosure.

Moreover, for example, as illustrated in FIG. 15, in a state where an introducer sheath C is inserted in the blood vessel, before the introducer sheath C is removed, a guide wire G is inserted into the introducer sheath C, and the embolization material k is pushed by the guide wire G and can be disposed on a blood vessel wall. The introducer sheath C is removed after the embolization material k is disposed.

Figure 16A:
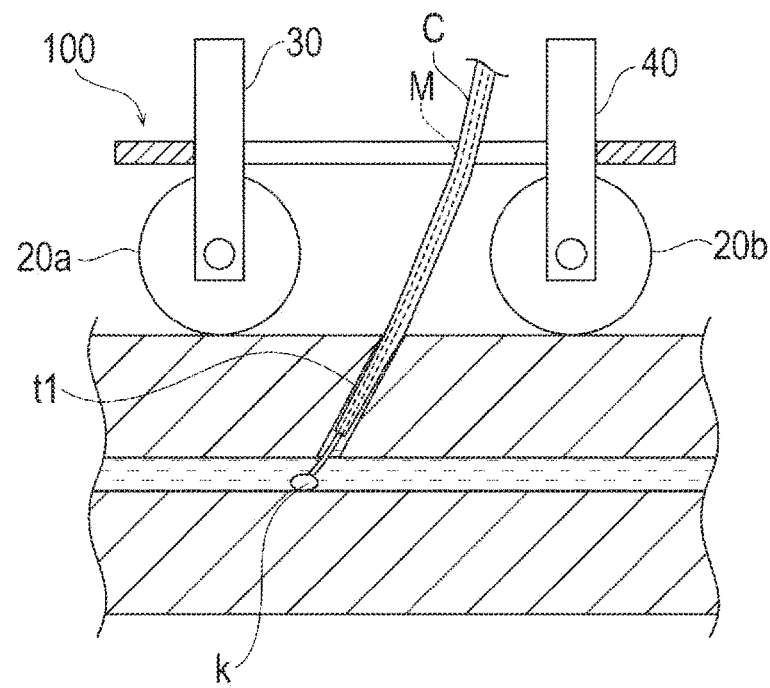
FIGS. 16A and 16B are cross-sectional views schematically illustrating an example of the hemostatic method using the hemostatic device according to the present disclosure.
Figure 16B:
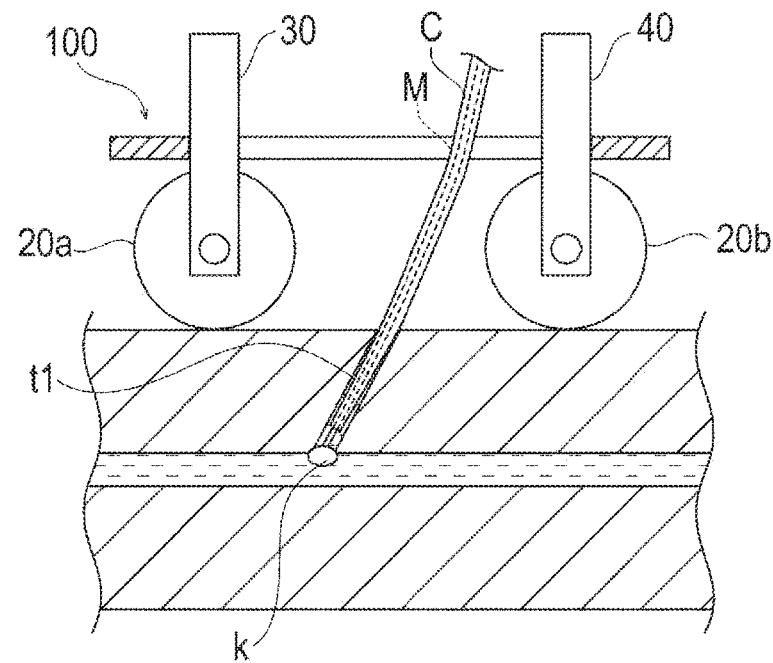

In addition, for example, as illustrated in FIG. 16A, before the introducer sheath C is removed, a flexible rod-shaped member M in which the embolization material k is applied to a distal end of the flexible rod-shaped member M is inserted into the introducer sheath C, and as illustrated in FIG. 16B, the embolization material k can be attached to the blood vessel wall. When the embolization material k is disposed, the embolization material k can be appropriately attached to the blood vessel wall by rotating the rod-shaped member M. The introducer sheath C is removed after the embolization material k is disposed in the blood vessel wall.

The operator can rather effectively increase the hemostasis effect by applying the embolization material k according to each method described above and then performing the hemostasis using the hemostatic device. According to the method illustrated in FIG. 15, FIG. 16A, or FIG. 16B, the hemostasis can be rapidly performed by closing the hole in the blood vessel wall using the embolization material k. Note that material properties, a nature (liquid, gel, or the like), or the like of the embolization material k is not limited. For example, as the embolization material k, it is possible to use a known biocompatible adhesive or the like.

Hereinbefore, the hemostatic device according to the present disclosure is described through the embodiments. However, the present disclosure is not limited to each of the described configurations, and can be appropriately modified based on descriptions in claims.

The detailed description above describes embodiments of a hemostatic device. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device configured to perform hemostasis on a puncture site of a subject, the hemostatic device comprising:
    a first support shaft and a first hemostatic member, the first support shaft configured to rotatably support the first hemostatic member;
    a second support shaft and a second hemostatic member, the second support shaft configured to rotatably support the second hemostatic member, the second hemostatic member being movable relatively close to or away from the first hemostatic member and configured to pinch a skin around the puncture site of the subject between the first hemostatic member and the second hemostatic member when the second hemostatic member moves toward the first hemostatic member, each of the first hemostatic member and the second hemostatic member includes a rotatable roller; and
    a plate-shaped member configured to be attached to a securing unit, the securing unit configured to secure the first hemostatic member and the second hemostatic member to a hand of the subject, and wherein the plate-shaped member includes a hole that receives the first hemostatic member and the second hemostatic member, and wherein the first hemostatic member and the second hemostatic member are movable within the hole to pinch the skin around the puncture site after the first hemostatic member and the second hemostatic member have contacted the skin of the subject.

2. The hemostatic device according to claim 1, wherein the rotatable rollers of the first hemostatic member and the second hemostatic member each includes a convex portion projecting radially in a circumferential direction.

3. The hemostatic device according to claim 1, further comprising:
    the securing unit configured to secure the first hemostatic member and the second hemostatic member to a hand of the subject.

4. The hemostatic device according to claim 3, wherein the securing unit includes a band-shaped member configured to be attachable to the hand of the subject.

5. The hemostatic device according to claim 3, wherein the securing unit includes a holding member configured to pinch the hand of the subject.

6. The hemostatic device according to claim 3, wherein the securing unit includes a projection portion on a side opposite to a portion in which the first hemostatic member and the second hemostatic member are disposed.

7. The hemostatic device according to claim 6, wherein the projection portion is attachable and detachable from the securing unit.

8. The hemostatic device according to claim 6, wherein the securing unit includes a holding member configured to pinch the hand of the subject.

9. The hemostatic device according to claim 6, wherein the securing unit includes a first holding portion and a second holding portion, the first holding portion and the second holding portion being pivotally connected to each other.

10. The hemostatic device according to claim 3, wherein the securing unit has a U-shaped cross-section, the first hemostatic member and the second hemostatic member being disposed on one end portion of the securing unit, and a projection portion on a side opposite to the one end portion of the securing unit in which the first hemostatic member and the second hemostatic member are disposed, and the projecting portion has a convex shape that projects toward a side of each of the first hemostatic member and the second hemostatic member.

11. The hemostatic device according to claim 1, further comprising:
an embolization material configured to be disposed in the puncture site of the subject.

12. A method for performing hemostasis on the puncture site of the subject with the hemostatic device according to claim 1, the method comprising:
moving the first hemostatic member toward the second hemostatic member, each of the first hemostatic member and the second hemostatic member including the rotatable roller; and
pinching the skin around the puncture site of the subject between the first hemostatic member and the second hemostatic member.

13. The method according to claim 12, comprising:
moving an outer side of each of the rotatable rollers of the first hemostatic member and the second hemostatic member toward one another; and
pinching the skin around the puncture site with the rotatable rollers of the first hemostatic member and the second hemostatic member.

14. The method according to claim 12, wherein the rotatable rollers of the first hemostatic member and the second hemostatic member each includes a convex portion projecting radially in at least a portion in a circumferential direction.

15. The method according to claim 12, further comprising:
securing the first hemostatic member and the second hemostatic member to a hand of the subject with a band-shaped member.

16. The method according to claim 12, further comprising:
securing the first hemostatic member and the second hemostatic member to a hand of the subject with a holding member configured to pinch the hand of the subject.

17. The hemostatic device according to claim 1, wherein the hole is configured to receive one or more of an applicator, an introducer sheath, and a guidewire.

18. A hemostatic device configured to perform hemostasis on a puncture site of a subject, the hemostatic device comprising:
a first support shaft and a first hemostatic member, the first support shaft configured to rotatably support the first hemostatic member;
a second support shaft and a second hemostatic member, the second support shaft configured to rotatably support the second hemostatic member, the second hemostatic member being movable relatively close to or away from the first hemostatic member and configured to pinch a skin around the puncture site of the subject between the first hemostatic member and the second hemostatic member when the second hemostatic member moves toward the first hemostatic member, each of the first hemostatic member and the second hemostatic member includes a rotatable roller;
an arm portion configured to contact and pinch the skin from an outer side of the rotatable rollers of the first hemostatic member and the second hemostatic member; and
a securing unit configured to secure the first hemostatic member, the second hemostatic member, and the arm portion to a hand of the subject.

19. A hemostatic device configured to perform hemostasis on a puncture site of a subject, the hemostatic device comprising:
a first hemostatic member, a second hemostatic member, and a third hemostatic member;
a support member configured to be located above the puncture site of the subject, and wherein the support member is a bent plate-shaped member configured to support the first hemostatic member, the second hemostatic member, and the third hemostatic member; and
an operation member configured to operate each of the first hemostatic member, the second hemostatic member, and the third hemostatic member in a radial direction, the operation member being a string-shaped operation member, each of the first hemostatic member, the second hemostatic member, and the third hemostatic member being connected to the string-shaped operation member, and configured when the string-shaped operation member is pulled, each of the first hemostatic member, the second hemostatic member, and the third hemostatic member move toward each other to pinch the skin around the puncture site, after the first hemostatic member, the second hemostatic member, and the third hemostatic member have contacted the skin of the subject, and when the string-shaped operation member is released, the operation member moves the first hemostatic member, the second hemostatic member, and the third hemostatic member away from each other.

20. The hemostatic device according to claim 19, wherein each of the first hemostatic member, the second hemostatic member, and the third hemostatic member is formed in a substantially spherical shape.

* * * * *